United States Patent [19]

Martin et al.

[11] 4,360,676
[45] Nov. 23, 1982

[54] 3,3,5-TRICHLOROGLUTARIC ACID IMIDE

[75] Inventors: Pierre Martin, Rheinfelden; Daniel Bellus̆, Riehen, both of Switzerland

[73] Assignee: Ciba-Geigy Corporation, Ardsley, N.Y.

[21] Appl. No.: 209,576

[22] Filed: Nov. 24, 1980

[30] Foreign Application Priority Data

Nov. 30, 1979 [CH] Switzerland ..................... 10661/79

[51] Int. Cl.$^3$ .......................................... C07D 211/38
[52] U.S. Cl. .................................... 546/243; 546/250; 546/294; 546/345; 260/465.4; 260/465.7
[58] Field of Search ................. 546/250, 345, 294, 243

[56] References Cited

U.S. PATENT DOCUMENTS

| | | | |
|---|---|---|---|
| 3,058,983 | 10/1962 | Johnson | 546/243 |
| 3,077,475 | 2/1963 | Johnson | 546/243 |
| 3,244,586 | 4/1966 | Rigterink | 260/959 X |
| 3,355,278 | 11/1967 | Weil | 71/113 X |
| 3,420,833 | 1/1969 | Taplin | 546/345 X |
| 3,538,100 | 11/1970 | Smith | 546/345 |
| 3,647,782 | 3/1972 | Collins | 546/243 X |
| 3,681,327 | 8/1972 | Newman | 546/243 X |
| 3,694,322 | 9/1972 | Ikeda | 203/79 X |
| 3,694,332 | 9/1972 | Parker | 546/345 X |
| 3,720,679 | 3/1973 | Feldman et al. | 546/243 |
| 3,751,421 | 8/1973 | Nyquist | 546/302 X |
| 3,849,422 | 11/1974 | Weis | 546/243 X |
| 3,993,654 | 11/1976 | Dean et al. | 546/345 |
| 4,133,675 | 1/1979 | Schurter et al. | 71/78 X |
| 4,225,716 | 9/1980 | Buhler et al. | 546/345 X |

FOREIGN PATENT DOCUMENTS

| | | |
|---|---|---|
| 1445683 | 1/1969 | Fed. Rep. of Germany ...... 546/345 |
| 2141632 | 4/1972 | Fed. Rep. of Germany . |
| 991526 | 5/1965 | United Kingdom . |
| 1024399 | 3/1966 | United Kingdom . |
| 1050378 | 12/1966 | United Kingdom ................ 546/345 |
| 1334922 | 10/1973 | United Kingdom . |

OTHER PUBLICATIONS

Mori, et al., C.A., 79, 31508g (1973).
Matsumoto, et al, C.A., 84, 73598v (1976).
Organic Synthesis, col. vol. 1, pp. 300–301. (2nd ed).
Chemical Reviews, 38, pp. 501, 514, 515, (1946).
Freidlina et al., Bull. Acad. Sci. USSR (1952), pp. 800–803—(Eng. Trans. 1959).
Martin et al., Helv. Chim. Acta. 63, pp. 1947–1957, (1980).
Den Hertog, Recueil Trav. Chim., 70 (1951), pp. 182–190.

Primary Examiner—Joseph Paul. Brust
Attorney, Agent, or Firm—Frederick H. Rabin

[57] ABSTRACT

3,3,5-Trichloroglutaric acid imide can be produced either by reacting a trichloroacetic acid alkyl ester, in the presence of a catalyst, with acrylonitrile to the corresponding 2,2,4-trichloro-4-cyanobutyric acid alkyl ester, converting this into the amide, and cyclizing the 2,2,4-trichloro-4-cyano-butanecarboxylic acid amide, in an aqueous acid medium, to the 3,3,5-trichloroglutaric acid imide; or by reacting trichloroacetonitrile, in the presence of a catalyst, to 2,2,4-trichloro-4-cyanobutyronitrile, and cyclizing this, in an aqueous acid medium, to 3,3,5-trichloroglutaric acid imide. The catalyst used for the addition reactions can be for example copper(I) chloride or copper(II) oxide. 3,3,5-Trichloroglutaric acid imide can be converted, by treatment with a dehydrating chlorinating agent, such as POCl$_3$, into the known 2,3,5,6-tetrachloropyridine, which for its part is used for producing various active substances, particularly insecticides, herbicides and fungicides.

1 Claim, No Drawings

3,3,5-TRICHLOROGLUTARIC ACID IMIDE

The present invention relates to 3,3,5-trichloroglutaric acid imide as a novel compound, to processes for producing it, and to its use for producing 2,3,5,6-tetrachloropyridine.

2,3,5,6-Tetrachloropyridine and 3,5,6-trichloropyridin-2-ol obtainable therefrom by hydrolysis are valuable intermediates for producing various active substances, particularly insecticides, herbicides and fungicides [cp. for example U.S. Pat. Nos. 4,133,675, 3,244,586, 3,355,278 and 3,751,421; French Patent Specification No. 2,171,939 and also J. Agr. Food Chem. 14, 304 (1966)]. The processes hitherto known for producing 2,3,5,6-tetrachloropyridine are in various respects unsatisfactory. 2,3,5,6-Tetrachloropyridine can be obtained by high-temperature chlorination of pyridine or of pyridine derivatives, such as 3,5-dichloro-2-trichloromethylpyridine and 2,6-dichloropyridine (about 200°–600° C., preferably about 350°–600° C.); by reaction of glutaric acid dinitrile with chlorine in the gaseous phase at elevated temperatures (about 400°–600° C.); or by chlorination of ε-caprolactam or cyclohexanone-oxime at elevated temperatures. There are formed however in these processes, besides the desired symmetrical tetrachloropyridine, a number of highly chlorinated pyridines, which have to be separated (cp. for example the British Patent Specifications Nos. 1,050,378, 1,334,922 and 991,526, the U.S. Pat. Nos. 3,420,833 and 3,538,100, and the German Offenlegungsschriften Nos. 1,445,683 and 2,141,632).

2,3,5,6-Tetrachloropyridine can be obtained also by stepwise chlorination of 6-bromo- or 6-chloro-2-ethoxypyridine [cp. Recueil trav. chim. 70, 182 (1951)]. A further possibility is to proceed with the high-temperature chlorination with excess chlorinating agent more or less selectively as far as pentachloropyridine, and to subsequently reduce the chlorine atom in the 4-position either with zinc (cp. for example U.S. Pat. No. 3,993,654) or electrolitically (cp. U.S. Pat. No. 3,694,332). In the case of reduction with zinc, there occur large amounts of zinc salts, a factor which is undesirable from an ecological standpoint. High-temperature chlorination, electrolytic reduction as well as the (electrolytic) generation of zinc necessitate on the other hand a high consumption of energy. The pentachloropyridine itself has moreover a relatively severe skin- and eye-irritating effect.

It has now been found that 3,3,5-trichloroglutaric acid imide can be produced with avoidance of the above-described disadvantages, in a simple, economical and ecologically favourable manner and with the use of readily accessible cheap starting products, either (a) by reacting a trichloroacetic acid alkyl ester of the formula I

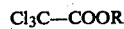  (I)

wherein R is alkyl having 1 to 6 carbon atoms, in the presence of a catalyst, with acrylonitrile to give a 2,2,4-trichloro-4-cyanoacetic acid alkyl ester of the formula II

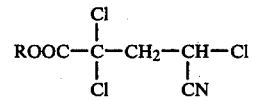  (II)

wherein R has the meaning given under the formula I, converting the compound of the formula II, in the presence of ammonia, into 2,2,4-trichloro-4-cyano-butanecarboxylic acid amide, and cyclising the 2,2,4-trichloro-4-cyano-butanecarboxylic acid amide, in an aqueous acid medium, to 3,3,5-trichloroglutaric acid imide; or (b) by reacting trichloroacetonitrile, in the presence of a catalyst, with acrylonitrile to 2,2,4-trichloro-4-cyanobutyronitrile, and cyclising the 2,2,4-trichloro-4-cyanobutyronitrile, in an aqueous acid medium, to 3,3,5-trichloroglutaric acid imide.

2,2,4-Trichloro-4-cyanobutyric acid alkyl ester of the formula II, 2,2,4-trichloro-4-cyano-butanecarboxylic acid amide and 2,2,4-trichloro-4 cyanobutyronitrile are novel compounds and likewise form subject matter of the present invention.

Alkyl groups R can be straight-chain or branched-chain and contain in particular 1 to 4 carbon atoms in the alkyl moiety. There is used particularly preferably as compound of the formula I the corresponding acetic acid methyl ester or acetic acid ethyl ester.

3,3,5-Trichloroglutaric acid imide can be subsequently converted in a simple manner, by treatment with a dehydrating chlorinating agent, into 2,3,5,6-tetrachloropyridine.

Catalysts which can be used for the addition reaction of the trichloracetic acid alkyl ester of the formula I or the trichloroacetonitrile with acrylonitrile in the process according to the invention are compounds known per se, such as metals of the main group VIII and of the subgroups VIa, VIIa, Ib and IIb of the periodic system (according to Lehrbuch der anorgan. Chemie [Textbook of inorganic Chemistry], Hollemann-Wiberg, W. de Gruyter Co., Berlin), for example iron, cobalt, nickel, ruthenium, rhodium, palladium, chromium, molybdenum, manganese, copper and zinc. These metals can be used in the elementary form or in the form of compounds. Suitable compounds of this type are for example oxides, halides, sulfates, sulfites, sulfides, nitrates, acetates, stearates, citrates, carbonates, cyanides and rhodanides, as well as complexes with ligands, such as phosphines, phosphites, benzoyl- and acetylacetonates, nitriles, isonitriles and carbon monoxide.

Examples which may be mentioned are: copper(II) oxide, iron(III) oxide; Cu(I)-, Cu(II)-, Fe(II)- and Fe(III)-bromides and -iodides and particularly -chlorides, zinc choride, as well as the chlorides of ruthenium, of rhodium, of palladium, of cobalt and of nickel; Cu(II)-sulfate, Fe(II)- and Fe(III)-sulfates; Cu(II) nitrate and iron(III) nitrate; manganese(III) acetate, copper(II)-acetate, copper(II) stearate, iron(III) citrate, Cu(I)-cyanide; ruthenium(II) dichloro-tris-triphenylphosphine, rhodium-dichloro-tris-triphenylphosphine; chromium- and nickel-acetylacetonate, copper(II) acetylacetonate, iron(III) acetylacetonate, cobalt(II)- and cobalt(III)-acetylacetonate, manganese(II) acetylacetonate, copper(II)-benzoylacetonate; iron carbonyl-cyclopentadienyl complex; molybdenum carbonylcyclopentadienyl complex, chromium-tricarbonylaryl complexes, ruthenium(II) acetate complex, chromium- and molybdenum-hexacarbonyl, nickel tetracarbonyl, iron pentacarbonyl and cobalt- and manganese-carbonyl.

It is also possible to use mixtures of the stated metals with metal compounds and/or other additives, such as copper powder in combination with one of the aforementioned copper compounds; mixtures of copper powder with lithium halides, such as lithium chloride, or with isocyanides, such as tert-butylisocyanide; mixtures of iron powder with iron(III) chloride, optionally with the addition of carbon monoxide; mixtures of iron(III) chloride and benzoin; mixtures of iron(II)- and iron-(III)-chloride and trialkylphosphites; and mixtures of iron pentacarbonyl and iodine.

Preferred catalysts are iron(III) oxide, iron(II)- and iron(III)-salts and -complexes, particularly iron(II)- and iron(III)-chloride, as well as iron powder; ruthenium-(III) chloride, ruthenium(II) dichloro-tris-triphenylphosphine, copper powder, copper bronze, copper(II) oxide, copper(I)-and copper(II)-salts and -complexes, such as Cu(I) chloride, Cu(II) chloride, Cu(I) bromide, Cu(II) bromide; Cu(II)-acetate, Cu(II) acetylacetonate, Cu(II) benzoylacetonate, Cu(II) sulfate, Cu(II) nitrate, Cu(I) cyanide and Cu(I) iodide.

Particularly preferred catalysts are copper(II) oxide, copper powder, copper bronze, copper(I)- and copper-(II)-chloride or -bromide and copper(I) iodide, as well as mixtures thereof.

The catalysts are generally used in amounts of about 0.01 to 10 mol %, preferably 0.1 to 5 mol %, relative to the acrylonitrile.

The reaction of acrylonitrile with the trichloroacetic acid alkyl ester of the formula I or with trichloroacetonitrile is advantageously performed in the presence of an organic solvent. Suitable organic solvents are those in which the catalysts are sufficiently soluble, or which can form complexes with the catalysts, which however are inert to the compound of the formula I or to the trichloroacetonitrile and to the acrylonitrile. Examples of such solvents are alkyl nitriles, particularly those having 2 to 5 carbon atoms, such as acetonitrile, propionitrile and butyronitrile; 3-alkoxypropionitriles having 1 or 2 carbon atoms in the alkoxy moiety, such as 3-methoxypropionitrile and 3-ethoxypropionitrile; aromatic nitriles, especially benzonitrile, also acrylonitrile (i.e. excess reagent as solvent); aliphatic alcohols having up to 6 carbon atoms, such as methanol, ethanol, propanol, isopropanol, butanols and pentanols; aliphatic ketones preferably having all together 3 to 8 carbon atoms, such as acetone, diethyl ketone, methylisopropyl ketone, diisopropyl ketone, methyl-tert-butyl ketone; alkyl and alkoxyalkyl esters of aliphatic monocarboxylic acids having all together 2 to 6 carbon atoms, such as formic acid-methyl and -ethyl esters, acetic acid-methyl, ethyl, -n-butyl and -isobutyl esters, as well as 1-acetoxy-2-methoxyethane; cyclic ethers, such as tetrahydrofuran, tetrahydropyrane and dioxane; N,N-dialkylamides of aliphatic monocarboxylic acids having 1 to 3 carbon atoms in the acid moiety, such as N,N-dimethylformamide, N,N-dimethylacetamide, N,N-diethylacetamide and N,N-dimethylmethoxyacetamide; ethylene glycol- and diethylene-glycol dialkyl ethers having 1 to 4 carbon atoms in each of the alkyl moieties, such as ethylene glycol dimethyl, -diethyl, and-di-n-butyl ethers; diethylene glycol diethyl and -di-n-butyl ethers; and hexamethylphosphoric acid triamide (hexametapol).

Particularly preferred solvents for the process variant (b) are alkyl nitriles having 2 to 5 carbon atoms, and 3-alkoxypropionitriles having 1 or 2 C atoms in the alkoxy moiety, especially acetonitrile, butyronitrile, 3-methoxypropionitrile and acrylonitrile, whilst for the process variant (a) there are also preferred aliphatic alcohols having up to 6 carbon atoms, particularly methanol and ethanol, as well as excess acrylonitrile.

The reaction temperatures for the addition reactions are in general between about 70° and 220° C., preferably between about 90° and 130° C., and they can be performed either in an open or closed vessel. It is particularly preferred to perform the addition reaction in a closed system at a pressure corresponding to the respective reaction temperature, the pressure being for example in the range of 0 to 50 bars.

The conversion of the 2,2,4-trichloro-4-cyanoacetic acid alkyl ester of the formula II, in the presence of ammonia, into the 2,2,4-trichloro-4-cyano-butanecarboxylic acid amide is performed in a manner known per se, preferably in an inert organic solvent, especially aliphatic alcohols having up to 6 carbon atoms, particularly methanol or ethanol. The conversion into the amide is performed generally at a temperature of between about 0° and 100° C., preferably between 0° and 50° C.

Cyclisation of 2,2,4-trichloro-4-cyanobutanecarboxylic acid amide or 2,2,4-trichloro-4-cyanobutyronitrile, in an aqueous acid medium, to 3,3,5-trichloroglutaric acid imide, and conversion thereof into 2,3,5,6-tetrachloropyridine (aromatisation with dehydration of the dicarboxylic acid imide functions and simultaneous splitting-off of HCl) can likewise be performed in a manner known per se [cp. for example Helv. Chim. Acta, 59, 179 (1976) and literature referred to therein]. The cyclisation reaction is advantageously performed at temperatures between about −10° and +120° C., preferably between about 60° and 110° C., and with the addition of acetic acid. The acids used can be for example concentrated hydrochloric acid, or preferably about 50–80% sulfuric acid. Suitable dehydrating chlorinating agents for the conversion of 3,3,5-trichloroglutaric acid imide into 2,3,5,6-tetrachloropyridine are for example: $PCl_3$, $PCl_5$, $POCl_3$, phenylphosphoric acid chloride and phosgene. A preferred chlorinating agent is $POCl_3$. The addition of catalytic amounts of N,N-dimethylformamide is advisable under certain circumstances.

The reaction temperatures are advantageously between about 50° and 200° C., particularly between about 100° and 180° C.

The aforementioned novel intermediates as well as the 3,3,5-trichloroglutaric acid imide and 2,3,5,6-tetrachloropyridine can be isolated in the customary manner and purified, for example by filtration, distillation, recrystallisation, and so forth.

As mentioned at the beginning of the text, 2,3,5,6-tetrachloropyridine (and 3,5,6-trichloropyridin-2ol which is obtainable therefrom) are suitable for producing various active substances.

EXAMPLE 1

Production of 3,3,5-trichloroglutaric acid imide of the formula

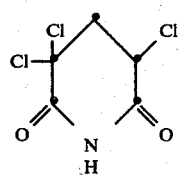

(a) 13 ml of 50% sulfuric acid are added to 26.0 g of 2,2,4-trichloro-4-cyano-butanecarboxylic acid amide and 105 ml of glacial acetic acid, and stirring is continued at 65° C. bath temperature until a solution is formed (about 5 minutes). This reaction solution is immediately poured onto ice, and after 1 hour it is filtered. The yield is 21.6 g of 3,3,5-trichloroglutaric acid imide; m.p. 158° to 159° C. IR Spectrum (CHCl$_3$): 1740 cm$^{-1}$ (CO); $^1$H-NMR spectrum (CDCl$_3$/DMSO-d$_6$) in ppm: 11.8 (board s, with D$_2$O interchangeable, NH); 4.87 (X part, J=6 and 12 Hz, CH); 3.26 (AB part, J=6 and 12 and 15 Hz, CH$_2$).

Elementary analysis for C$_5$H$_6$Cl$_3$NO$_2$ (molecular weight 216.46): calculated: C 27.75% H 1.86% N 6.46% Cl 49.15%. found: C 27.78% H 1.84% N 6.52% Cl 49.21%.

The 2,2,4-trichloro-4-cyanobutanecarboxylic acid amide used in the above Example is produced as follows: 300 ml of trichloroacetic acid ethyl ester, 176 ml of acrylonitrile, 7 g of CuO and 500 ml of ethanol are held at 120° C. for 20 hours. The reaction mixture is concentrated by evaporation, taken up in benzene, filtered clear and again concentrated by evaporation, and the residue obtained is distilled. The result is 234.5 g of 2,2,4-trichloro-4-cyanoacetic acid ethyl ester, b.p. 85° C./5 Pa.

$^1$H-NMR Spectrum (CDCl$_3$) in ppm: 4.93 (X part, J=6 and 7 Hz, CH); 4.4 (q, J=7 Hz, CH$_2$); 3.35 (AB part, J=6 and 7 and 15 Hz, CH$_2$); 1.48 (t, J=7 Hz, CH$_3$).

70.2 g of the above ester are placed together with 84 ml of ammonium hydroxide solution (25%) and 150 ml of methanol at 0° C., and the whole is stirred for 5 hours at room temperature. The reaction mixture is subsequently cooled to 0° C. and filtered, and the precipitate is washed with water and dried to thus obtain 2,2,4-trichloro-4-cyano-butanecarboxylic acid amide; m.p. 178° C.

Elementary analysis for C$_5$H$_5$Cl$_3$N$_2$O (molecular weight 201.47): calculated: C 28.0% H 2.35% Cl 49.2% N 13.05%. found: C 27.81% H 2.37% Cl 49.29% N 12.99%.

(b) 20.0 g of 2,2,4-trichloro-4-cyanobutyronitrile with 70 ml of glacial acetic acid and 16 ml of 78% sulfuric acid are refluxed for 2 hours. The reaction solution is poured onto ice, stirred and subsequently extracted with methylene chloride. After drying with magnesium sulfate and concentration of the extract by evaporation, the solid residue is digested with diethyl ether. There is obtained 3,3,5-trichloroglutaric acid imide; m.p. 158°–159° C., the spectroscopic data of which are identical to those of the imide described under (a).

The 2,2,4-trichloro-4-cyanobutyronitrile used in the above Example is produced as follows: 53.1 g of acrylonitrile, 433.2 g of trichloroacetonitrile, 7 g of copper (I) chloride and 300 ml of acetonitrile are held in an enamel autoclave at 115° C. for 24 hours. The reaction mixture is then filtered clear and concentrated by evaporation. The residue is distilled to yield 145 g of 2,2,4-trichloro-4-cyanobutyronitrile; b.p. 78° C./65 Pa.

$^1$NMR Spectrum (CDCl$_3$) in ppm: 4.87 (X part, J=6 and 6.5 Hz, CH); 3.30 (AB part, J=6 and 6.5 and 16 Hz, CH$_2$).

Elementary analysis for C$_5$H$_3$Cl$_3$N$_2$ (molecular weight 197.5): calculated: C 30.41% H 1.54% N 14.18% Cl 53.85%. found: C 29.9% H 1.6% N 13.8% Cl 54.1%.

EXAMPLE 2

4.3 g of 3,3,5-trichloroglutaric acid imide and 80 ml of phosphorus oxychloride are held for 12 hours at 170° C.; the reaction mixture is subsequently poured onto ice and stirred. The yield after extraction with benzene, drying over magnesium sulfate and treatment with active charcoal is 3.65 g of 2,3,5,6-tetrachloropyridine; m.p. 86°–88° C.

EXAMPLE 3

19.2 g of 3,3,5-trichloroglutaric acid imide and 100 ml of phosphorous oxychloride are held at 180° C. for 3 hours. The excess phosphorous oxychloride is distilled off, and the residue is distilled with steam. The product obtained after drying over phosphorous oxide is 2,3,5,6-tetrachloropyridine, m.p. 89°–90° C.

EXAMPLE 4

12.4 g of 3,3,5-trichloroglutaric acid imide are introduced portionwise into a solution of 50 ml of N,N-dimethylformamide and 25 g of PCl$_5$. The mixture is heated to 100° C., whereupon the reaction temperature rises to 160° C. The reaction mixture after cooling is decomposed with ice, and stirred for 3 hours. The precipitate is filtered off, washed with water, and recrystallised from methanol to thus obtain 2,3,5,6-tetrachloropyridine; m.p. 86°–88° C.

What is claimed is:
1. 3,3,5-Trichloroglutaric acid imide.

* * * * *